(12) United States Patent
Schutz et al.

(10) Patent No.: US 8,211,026 B2
(45) Date of Patent: Jul. 3, 2012

(54) FINGER MOUNTED PROBE ADAPTED FOR INTRAOPERATIVE USE

(75) Inventors: Ronald W. Schutz, Portland, OR (US); Scott S. Corbett, III, Portland, OR (US); Kenneth N. Bates, Beaverton, OR (US); William McDonough, Portland, OR (US); Albert H. Krause, Vancouver, WA (US)

(73) Assignee: Blacktoe Medical III, Inc., Portland, OR (US)

( * ) Notice: Subject to any disclaimer, the term of this patent is extended or adjusted under 35 U.S.C. 154(b) by 102 days.

(21) Appl. No.: 11/895,607

(22) Filed: Aug. 24, 2007

(65) Prior Publication Data

US 2008/0300488 A1    Dec. 4, 2008

Related U.S. Application Data

(63) Continuation-in-part of application No. 10/863,644, filed on Jun. 8, 2004, now abandoned, which is a continuation-in-part of application No. 10/724,382, filed on Nov. 26, 2003, now Pat. No. 7,297,115.

(60) Provisional application No. 60/923,323, filed on Apr. 13, 2007, provisional application No. 60/429,614, filed on Nov. 27, 2002.

(51) Int. Cl.
    *A61B 8/00* (2006.01)
(52) U.S. Cl. .......... 600/459; 600/437; 600/462
(58) Field of Classification Search .......... 73/1.82, 73/596; 600/407, 437, 459, 462
    See application file for complete search history.

(56) References Cited

U.S. PATENT DOCUMENTS

| | | | |
|---|---|---|---|
| 4,003,621 A | 1/1977 | Lamp | |
| 4,250,894 A | 2/1981 | Frei et al. | |
| 4,407,295 A | 10/1983 | Steuer et al. | |
| 4,545,386 A | 10/1985 | Hetz et al. | |
| 4,671,292 A | 6/1987 | Matzuk | |
| 4,693,529 A | 9/1987 | Stillie | |
| 4,779,244 A | 10/1988 | Horner et al. | |
| 4,913,656 A | 4/1990 | Gordon et al. | |
| 4,940,413 A | 7/1990 | Childers et al. | |
| 4,972,839 A | 11/1990 | Angelsen | |
| 5,026,291 A | 6/1991 | David | |
| 5,088,500 A | 2/1992 | Wedel et al. | |
| 5,123,852 A | 6/1992 | Gillett | |
| 5,152,293 A | 10/1992 | Vonesh et al. | |
| 5,195,519 A | 3/1993 | Angelsen | |
| 5,199,881 A | 4/1993 | Oshita et al. | |
| 5,265,329 A | 11/1993 | Jones et al. | |
| 5,284,147 A | 2/1994 | Hanaoka et al. | |
| 5,351,691 A * | 10/1994 | Brommersma | 600/462 |

(Continued)

OTHER PUBLICATIONS

International Search Report of PCT/US03/38182, dated Oct. 25, 2005, 3 pgs.

(Continued)

*Primary Examiner* — Tse Chen
*Assistant Examiner* — Peter Luong
(74) *Attorney, Agent, or Firm* — Lane Powell PC; Brenna K. Legaard

(57) ABSTRACT

An ultrasound finger-mounted probe that has a finger clip that is adapted to be mounted on a human finger. The finger clip also has an interior surface adapted to contact the human finger. An ultrasound probe is adapted to be supported by the finger clip. Also, the ultrasound probe protrudes outwardly, relative to the interior surface, by less than 1.5 cm.

16 Claims, 9 Drawing Sheets

U.S. PATENT DOCUMENTS

| | | |
|---|---|---|
| 5,372,512 A | 12/1994 | Wilson et al. |
| 5,381,795 A | 1/1995 | Nordgren et al. |
| 5,385,477 A | 1/1995 | Vaynkof et al. |
| 5,403,194 A | 4/1995 | Yamazaki |
| 5,413,107 A | 5/1995 | Oakley et al. |
| 5,452,717 A | 9/1995 | Branigan et al. |
| 5,461,482 A | 10/1995 | Wilson et al. |
| 5,482,047 A | 1/1996 | Nordgren |
| 5,505,205 A | 4/1996 | Solomon et al. |
| 5,533,904 A | 7/1996 | Nobel et al. |
| 5,573,409 A | 11/1996 | Shiley et al. |
| 5,597,982 A | 1/1997 | Hiwada |
| 5,598,194 A | 1/1997 | Hall et al. |
| 5,598,846 A | 2/1997 | Peszynski |
| 5,604,976 A | 2/1997 | Stobie et al. |
| 5,630,419 A | 5/1997 | Ranalletta |
| 5,671,747 A | 9/1997 | Connor |
| 5,678,551 A | 10/1997 | Stevens |
| 5,752,517 A | 5/1998 | Harman |
| 5,782,645 A | 7/1998 | Stobie et al. |
| 5,795,299 A | 8/1998 | Eaton et al. |
| 5,805,424 A | 9/1998 | Purinton |
| 5,805,425 A | 9/1998 | Peterson |
| 5,805,426 A | 9/1998 | Merritt et al. |
| 5,810,733 A | 9/1998 | Van Creveld et al. |
| 5,818,700 A | 10/1998 | Purinton |
| 5,846,097 A | 12/1998 | Marian, Jr. |
| 5,904,580 A | 5/1999 | Kozel et al. |
| 5,913,688 A | 6/1999 | Marian, Jr. |
| 6,024,579 A | 2/2000 | Bennett |
| 6,029,530 A | 2/2000 | Patton et al. |
| 6,052,286 A | 4/2000 | Worthen et al. |
| 6,097,033 A | 8/2000 | Brand |
| 6,106,305 A | 8/2000 | Kozel et al. |
| 6,117,084 A | 9/2000 | Green |
| 6,123,551 A | 9/2000 | Westfall |
| 6,182,341 B1 | 2/2001 | Talbot et al. |
| 6,309,358 B1 | 10/2001 | Okubo |
| 6,350,132 B1 | 2/2002 | Glatts, III |
| 6,358,064 B2 | 3/2002 | Szalay et al. |
| 6,671,531 B2 | 12/2003 | Al-Ali et al. |
| 6,726,635 B1 | 4/2004 | LaSala |
| 6,746,402 B2 | 6/2004 | Ustuner |
| 6,780,154 B2 | 8/2004 | Hunt et al. |
| 7,037,270 B2 | 5/2006 | Seward |
| 2001/0031923 A1 | 10/2001 | Seward et al. |
| 2004/0111029 A1* | 6/2004 | Bates et al. ............... 600/437 |
| 2004/0225217 A1 | 11/2004 | Voegele et al. |
| 2005/0085731 A1 | 4/2005 | Miller et al. |
| 2005/0096554 A1 | 5/2005 | Dudik et al. |

OTHER PUBLICATIONS

Stanton, Robert E., *High-Density Pad Grid Array Interconnect System*, AMP Journal of Technology, Nov. 3, 1993, 6 pgs., vol. 3, U.S.

* cited by examiner

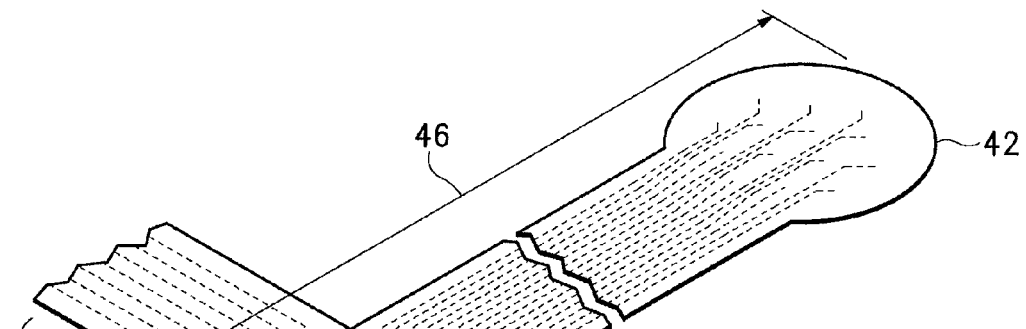
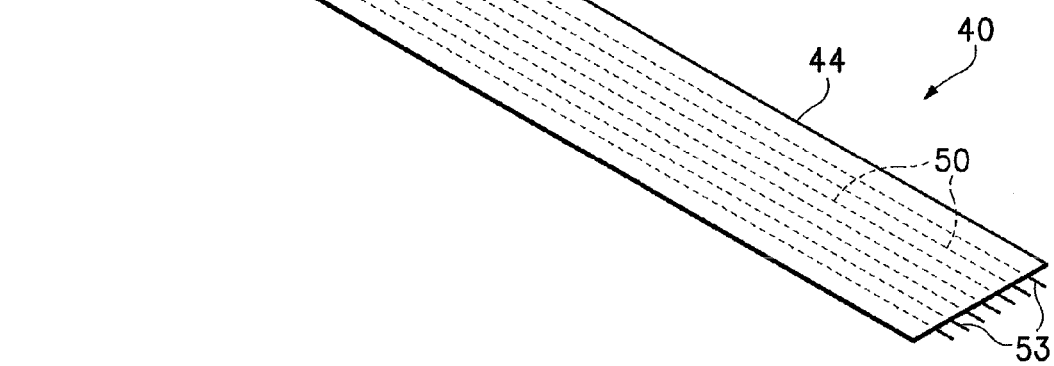
FIG.5A
FIG.5B

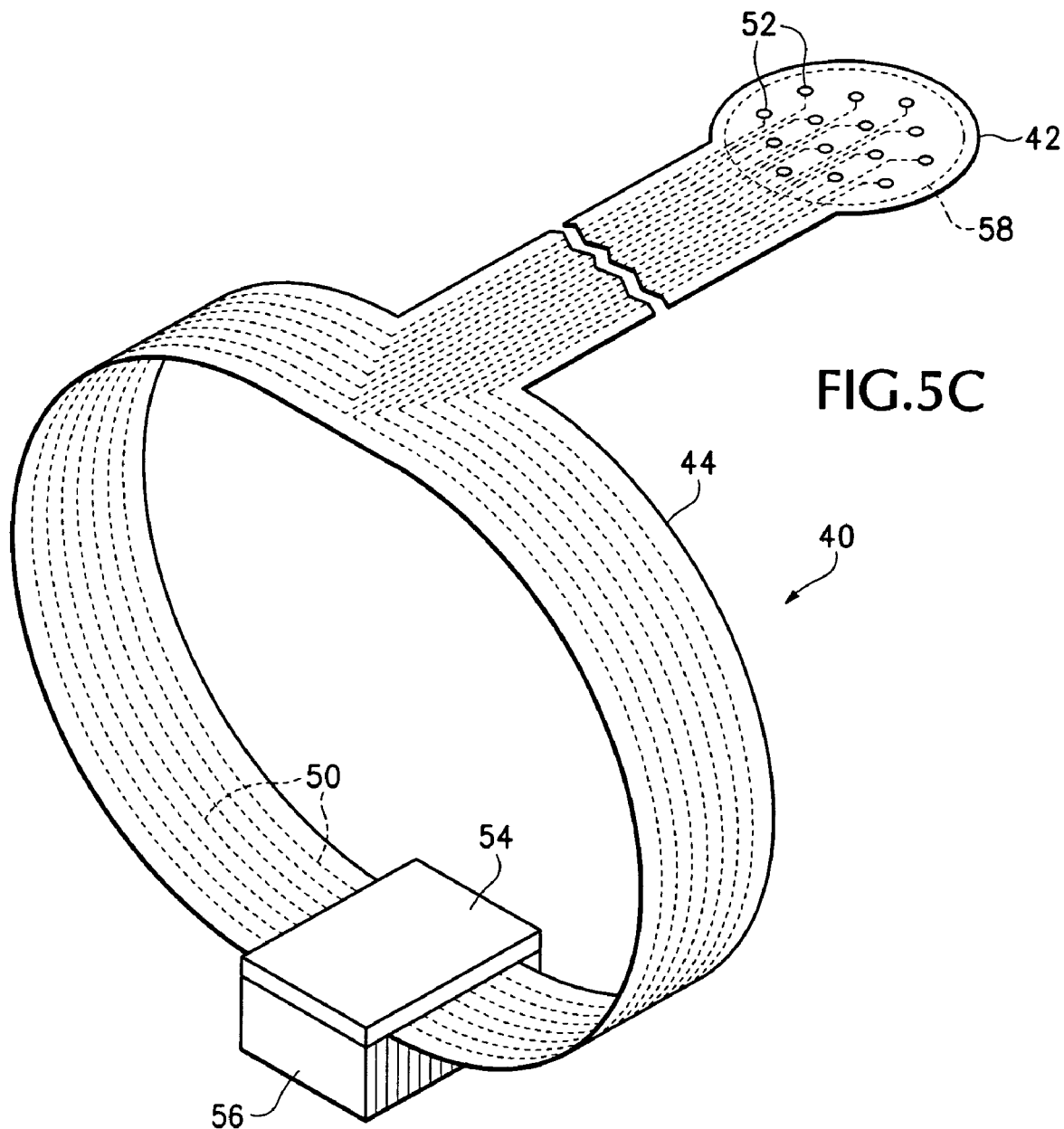

FINGER MOUNTED PROBE ADAPTED FOR INTRAOPERATIVE USE

CROSS REFERENCE TO RELATED APPLICATIONS

This application claims the benefit of the filing date of provisional application Ser. No. 60/923,323 filed Apr. 13, 2007, and is a continuation-in-part of application Ser. No. 10/863,644 filed Jun. 8, 2004, now abandoned, both of which are incorporated herein by reference as if fully set forth herein; application Ser. No. 10/863,644 is a continuation-in-part of application Ser. No. 10/724,382, filed Nov. 26, 2003, now U.S. Pat. No. 7,297,115, issued Nov. 20, 2007, and claims the benefit of the filing date of provisional application No. 60/429,614, filed Nov. 27, 2002.

This invention was made with government support under contract number W81XWH-07-2-0072 awarded by the U.S. Army Medical Research and Materiel Command. The government has certain rights in the invention.

BACKGROUND OF THE INVENTION

During a surgical procedure the timely acquisition of ultrasound imagery can mean the difference between life and death for the patient. Many devices and techniques have been developed or suggested to facilitate the speedy acquisition of ultrasound data, including laparoscopic ultrasound probes, finger mounted probes and hand-held probes having the ability to wirelessly transmit image data. Unfortunately, a number of problems continue to hamper medical personnel in the use of these devices.

For a hand held probe, users must take an extra mental step to remember and account for the distance between the position of the sensor head and the position of the user's hand. Frequently, the user is required to perform many mental tasks simultaneously, such as reviewing imagery; manipulating the probe to effect delicate changes in the probe pressure and angle; and accessing a bank of medical knowledge in an effort to diagnose a medical problem. During the stress of a medical procedure the task of mentally calculating the probe position and orientation, based on knowledge of the probe geometry, is an extra task that taxes the already highly-taxed mental resources of the medical professional. In addition, the extra displacement of the hand from the target probe head position reduces the ability to utilize muscle memory for probe positioning.

Another problem is the disassociation, both in time and location, of the tactile input that a medical professional receives from his fingers, during a procedure, and the ultrasound imagery data. For example, for situations in which a medical procedure must be interrupted for imaging to occur, it may be quite difficult for the surgeon to match the tactile information that he notes with the imagery previously acquired. In diagnostic procedures, it may be impossible for the medical professional to gain both tactile information and image information simultaneously. The task of remembering and piecing together the two types of data presents an additional challenge to the medical professional.

Yet another problem encountered by users of currently available probes is the difficulty in fitting a probe into a small area. The human body is largely composed of delicate tissue, and the object of the medical professional is often to address a localized medical problem while disturbing surrounding or intervening tissue as little as possible. For example, one type of desired imagery that is currently very difficult to acquire is imagery from the posterior of the heart. Hand held probes and/or probes having a large cross-section present a particular difficulty when it is desirable to move the probe head through body tissue in order to obtain imagery of interest.

Still another issue presented by currently available probes is the awkwardness of use, as the probe is typically tethered by a multi-conductor coaxial cable that is one to three meters long, to an imaging station. It is typically difficult to twist this cable, so rotating the probe about its longitudinal axis may prove difficult. In addition, the heavy weight of the cable and need to grip the probe handle have the potential to create repetitive motion injuries to sonographers and physicians who use the ultrasound probe.

Moreover, many of the tools available for imaging the internal regions of the human body may be unavailable in a particular case, due to special conditions. For example, although trans-esophageal imaging is an extremely valuable tool for cardiac surgeons, there are instances in which the esophagus is diseased, making it potentially harmful to insert a probe into the esophagus. In these situations, having some other method of imaging would be invaluable.

A problem faced specifically by cardiothoracic surgeons is that of assessing plaque deposits in a portion of the aortic arch and ascending aorta prior to accessing the portion of the aorta. If there are plaque deposits in the part of the aorta accessed, the deposit or a portion of it may break off, travel through the blood stream and lodge in a blood vessel, causing great damage to tissue that is dependent on the vessel for its blood supply. Although Doppler ultrasound probes are currently used for the assessment of plaque deposits in the aortic arch and ascending aorta, currently available intra-operative probes are about 10 cm long and rigid, for accessing interior portions of the body. Although this is potentially useful in some situations, it greatly complicates the task of successfully placing the probe for imaging a blood vessel and as in so many other intra-operative situations, permitting the user to maintain a correct sense for the orientation and position of the probe transducer.

Another issue faced by cardiothoracic surgeons is that of finding coronary arteries in a difficult-to-assess patient. Although in many patients the coronary arteries run close to or on the surface of the heart, in perhaps 10% of patients one or more coronary arteries are buried in cardiac tissue. This can create a serious problem for a cardiothoracic surgeon attempting to perform a bypass operation, in finding the correct artery. In a few unfortunate cases, an artery has been misidentified, leading to negative surgical results.

Moreover, the current configuration consisting of a permanently attached probe connected to a cable presents sterility issues. The cable typically could be autoclaved, but the sensor is too delicate. The entire sensor and cable assembly, however, is rather bulky for fitting into a bath of disinfecting liquid and the connector is typically not designed to be immersed in disinfectant. As a result, achieving satisfactory sterility of the probe and cable assembly can present a challenge to hospital personnel.

Moreover, changing the command to the sensor head, for example increasing or decreasing power, or changing the field of view of the scan or the frequency transmitted for typical current systems requires an adjustment at the imaging station, which is awkward for a medical professional in the middle of a procedure.

Although finger-mounted probes are currently known, they are typically either bulky and inflexible or they do not form precise imagery.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first, separate aspect, the present invention may take the form of an ultrasound finger-mounted probe that has a finger clip that is adapted to be mounted on a human finger. The finger clip also has an interior surface adapted to contact the human finger. An ultrasound probe is adapted to be supported by the finger clip. Also, the ultrasound probe protrudes outwardly, relative to the interior surface, by less than 1.5 cm.

In a second, separate aspect, the present invention is an ultrasound finger-mounted probe that has a finger clip that is adapted to be mounted on a human finger. An ultrasound probe is supported by the finger clip and has a front and a back and a lower surface. Also, the outermost surface protrudes increasingly outwardly, from front to back, at an average slope of less than 50°, thereby helping to avoid tissue damage when the probe is pushed through body tissue.

In a third separate aspect, the present invention is an ultrasound finger probe assembly that has a connector-half adapted to mate to a user-worn mating connector-half; a multi-conductor cable, electrically connected to the connector-half; a finger clip, adapted to be mounted on a human finger; and a finger probe supported by the finger clip. Additionally, the ultrasound finger probe assembly has a mass of less than 280 grams.

In a fourth separate aspect, the present invention is an ultrasound finger probe assembly that includes a distal 3 cm portion of the probe assembly. This distal 3 cm portion includes a finger clip, adapted to be mounted on a human finger and an ultrasound transceiver supported by the finger clip. Also, the distal 3 cm portion of the ultrasound probe assembly has a mass of less than 100 grams.

In a fifth separate aspect, the present invention is a method of performing intraoperative imaging that uses a finger mounted ultrasound probe assembly having a finger clip, adapted to be mounted on a human finger and that has an interior surface adapted to contact the human finger, and an ultrasound probe, supported by the finger clip. The ultrasound probe protrudes outwardly, relative to the interior surface, by less than 1.5 cm. A communications and display assembly is adapted to communicate information gathered from the probe, process the information and display the information. The probe assembly is placed on a surgeon's finger and used during a surgical operation.

In addition to the exemplary aspects and embodiments described above, further aspects and embodiments will become apparent by reference to the drawings and by study of the following detailed descriptions.

BRIEF DESCRIPTION OF THE DRAWINGS

FIG. 5A is a perspective view of a work piece representing a first step in a manufacturing process for the finger probe that is part of the assembly of FIG. 1.

FIG. 5B is a perspective view of a work piece representing a second step in a manufacturing process for the finger probe that is part of the assembly of FIG. 1.

FIG. 5C is a perspective view of a work piece representing a final step in a manufacturing process for the finger probe that is part of the assembly of FIG. 1.

DETAILED DISCUSSION OF THE PREFERRED EMBODIMENT

Figure 1:
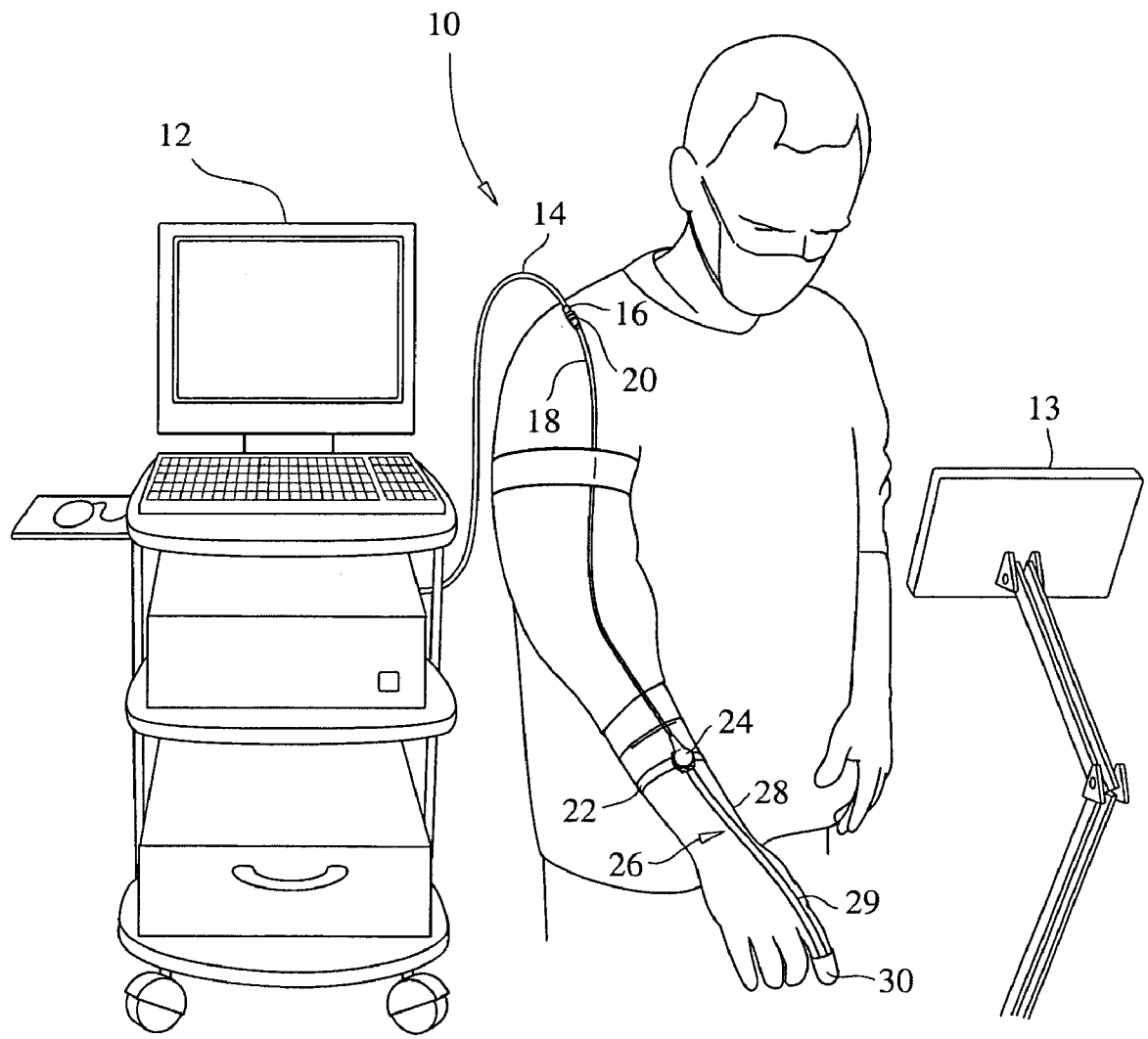
FIG. 1 is a perspective view of a probe assembly according to the present invention, shown in its environment, attached to a medical professional and ready for use.

In a first preferred embodiment, the present invention takes the form of an ultrasound imaging assembly 10. This assembly includes an imaging station 12, which can include an auxiliary display 13, for the user's convenience. Also, a first multi-conductor electrical cable 14 is electrically attached to the imaging station and terminates at a distal connector-half 16. A second multi-conductor cable 18 extends from a shoulder mounted connector half 20, which mates to the distal connector half 16 and terminates at a wrist or forearm band 22 that supports a forearm mounted connector-half 24. A finger probe sub-assembly 26 includes a finger probe sub-assembly connector-half 28 that mates with the forearm mounted connector-half 24. A cable in the form of a ribbon 29 extends from connector-half 28 to a finger-mounted probe 30.

In use, surgery may begin with the surgeon wearing the wrist band 22, which retains connector-half 24 and cable assembly 18, which includes shoulder mounted connector 20. At this stage it is possible that no finger probe sub-assembly 26 would be attached to cable 18 and that no station cable 14 would be connected to assembly 18, so that the user would be free to move about freely. This would also permit the surgeon full use of his hands while making an initial incision and further initial surgical cutting. When the area of interest in the patient's body has been accessed, the surgeon can take a sub-assembly 26, that has been kept ready for use, attach it to connector-half 24 and also have cable assembly 18 connected to imaging station 12, by way of cable 14 and connector-halves 16 and 20. This technique would destroy the sterility of the performing person's hands, so it is advisable that a person not otherwise participating in the surgery connect cable 18 to cable 14. Alternatively, a person having sterile hands could briefly don sterile gloves to effect the connection and then doff the gloves after finishing. In yet another possibility, the cable 14 is equipped with a sheath, which can be broken away and which is sterile underneath.

Figure 2:
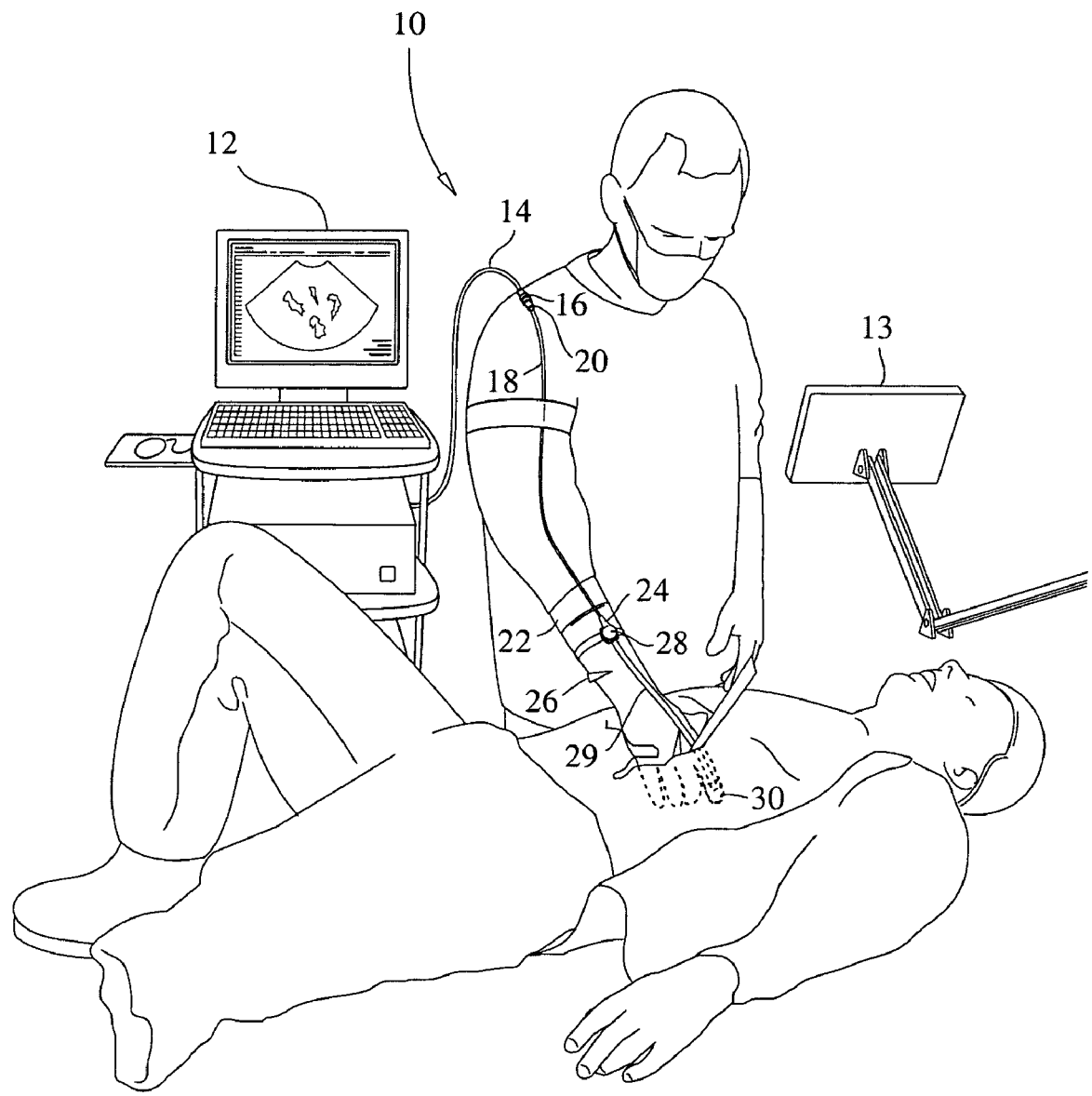
FIG. 2 is a perspective view of the probe assembly of FIG. 1, in use on a patient.

The surgeon can then introduce his hand, with the probe 30 attached, into the patient in order to gather imagery, as shown in FIG. 2. After the imagery is gathered, yielding an enhanced knowledge of the problem being addressed, sub-assembly 26 can be removed and detached from connector-half 24, to free the surgeon to continue his procedure. Later on, when further imagery is required, either the same sub-assembly 26 may be reattached or another sub-assembly 26, maintained in sterility can be attached to perform the further imaging. In a preferred embodiment, various probe configurations are kept at the ready, to provide the surgeon with a variety of image gathering options. This set of probes could vary in transmit frequency also, so that a first probe permits detailed imaging of fine structures, by using a relatively high frequency (@10-20 MHz), and a second lower resolution probe permits imaging of deeper structures using a lower ultrasound frequency (@2-10 MHz). Probes of various shapes and architectures are also made available to permit varying field of views. For example a curved linear array with relatively small radius of curvature permits imaging in the near field of the probe over a wide field of view. A phased array transducer permits imaging over a wide field of view at some distance from the array, while allowing imaging through a narrow access. A linear array permits imaging over a narrower field of view but provides good imaging of structures near the surface of the array. This is frequently the type of imagery that is highly desirable in surgical situations.

The use of a linear array in a finger mounted probe can be particularly advantageous. The probe can be configured so that the linear array images a scan plane that is parallel to the length dimension of the finger, or in another configuration, transverse to the finger. For the parallel configuration a portion of the scan looks forward from the finger, so that if the user directs his finger to point at the body surface, the probe will image a scan plane into the body. The user can then rotate the image plane by twisting his wrist, something that is quite easy for most users to do. In the case of a curved linear array, the curved surface permits a user to rock the probe on the body or organ surface in order to view tissue over a variety of contact angles. This is particularly easy to do using a finger mounted probe, as the index finger has a good freedom of movement in several axes. The transverse mounted probe has the advantage that it permits a physician to begin his examination with his hand transverse to the length of the patient's torso, which is a more natural position than parallel to the length of the patient's torso. A straight linear array or a phased array, however, has the advantage that the probe head profile can potentially be minimized, which is very important in accessing body portions.

The probe assembly 10 is also very useful in non-surgical procedures, for example, examination of a patient by imaging through the body surface, at the same time the physician is gathering tactile information. For example, the physician may wish to examine a bump or discolored area on the patient's skin and could by use of assembly 10 gather imagery at the same time he touches the abnormal area to diagnose the nature of the problem. Additionally, the user can make a fuller use of his muscle memory and positional awareness to return the probe head to the same location used in a recent probe use.

Probe assembly 10 is also used for exploration of body cavities, such as the vagina, rectum or mouth. Again, the user could both gain tactile information about an organ, such as the prostate gland at the same time he is gaining image information.

A physician may use assembly 10 to view difficult-to-access areas within the body, during surgery. For example during open heart surgery, the surgeon could move the probe 30 around to the posterior of the heart to gain imagery of heart features, such as valves that are difficult to otherwise image. This would be extremely difficult with a rigid probe that is poorly shaped for moving though tissue. A probe without advantageous physical characteristics could easily damage a patient during this type of use.

Referring to FIG. 2, in an additional example, assembly 10 can be used in an army field hospital to assist a surgeon in the task of removing shrapnel from a wounded soldier. Although an initial evaluation of the shrapnel locations could be made by an assessment of the entry wounds and pre-surgical imaging, a great deal might still not be known about the specific locations and dimensions of the individual pieces of shrapnel. After making an initial incision near an entry wound, the surgeon attaches a sub-assembly 26 to connector-half 24 and introduces the finger mounted probe 30 into the incision, to gain a further indication of the shrapnel positions. After gaining this information, the surgeon can quickly remove sub-assembly 26, so that he can have the full use of both hands in the task of removing pieces of shrapnel identified by the imaging. Later on during the same surgery, the surgeon may wish to take further images and may reattach sub-assembly 26, or some other sub-assembly 26, either for the sake of sterility or for the sake of having different imaging characteristics.

In another possible application, the low profile of probe 30 lends itself to imaging a premature infant in a neo-natal incubator, by reaching through the small entry orifice of the incubator. This action is difficult to do with currently available ultrasound probes.

The system described above, having cables 14, 18 and probe sub-assembly 26 has advantages both in providing a broad range of connectivity and in easing the task of maintaining a sterile operating theater. In a preferred embodiment, cable 18 may be sterilized in an autoclave without being damaged. Cable 14 is typically far enough removed from the sterile area so that it can be wiped down with disinfectant between instances of use. Probe sub-assembly 26 can be submerged in disinfectant fluid for sterilization. In an alternative embodiment, cable 18 is protected by a sterile sheath, which can be removed when a physician, who is wearing cable 18, needs to move to a different imaging station 12 and use a different probe assembly 26. In another alternative, probe assembly 26 is elongated, so that cable 18 does not have to extend as far toward probe 30, thereby making it more likely for cable 18 to avoid contamination from body fluids.

Also, cable 18 may be a universal unit, fitting to a broad range of probe makes, by having a super-set of pins, not all of which are used for any particular sub-assembly 26. An adapter is provided that would be interposed between cable 18 and imaging station 12, either where cable 18 connects to cable 14, where cable 14 connects to station 12, or as part of cable 14. A different adapter is necessary for each make of imaging station 12. It should be noted that this feature of system 10 can be used to increase the usability for ultrasound probes that are not finger probes.

Figure 3:
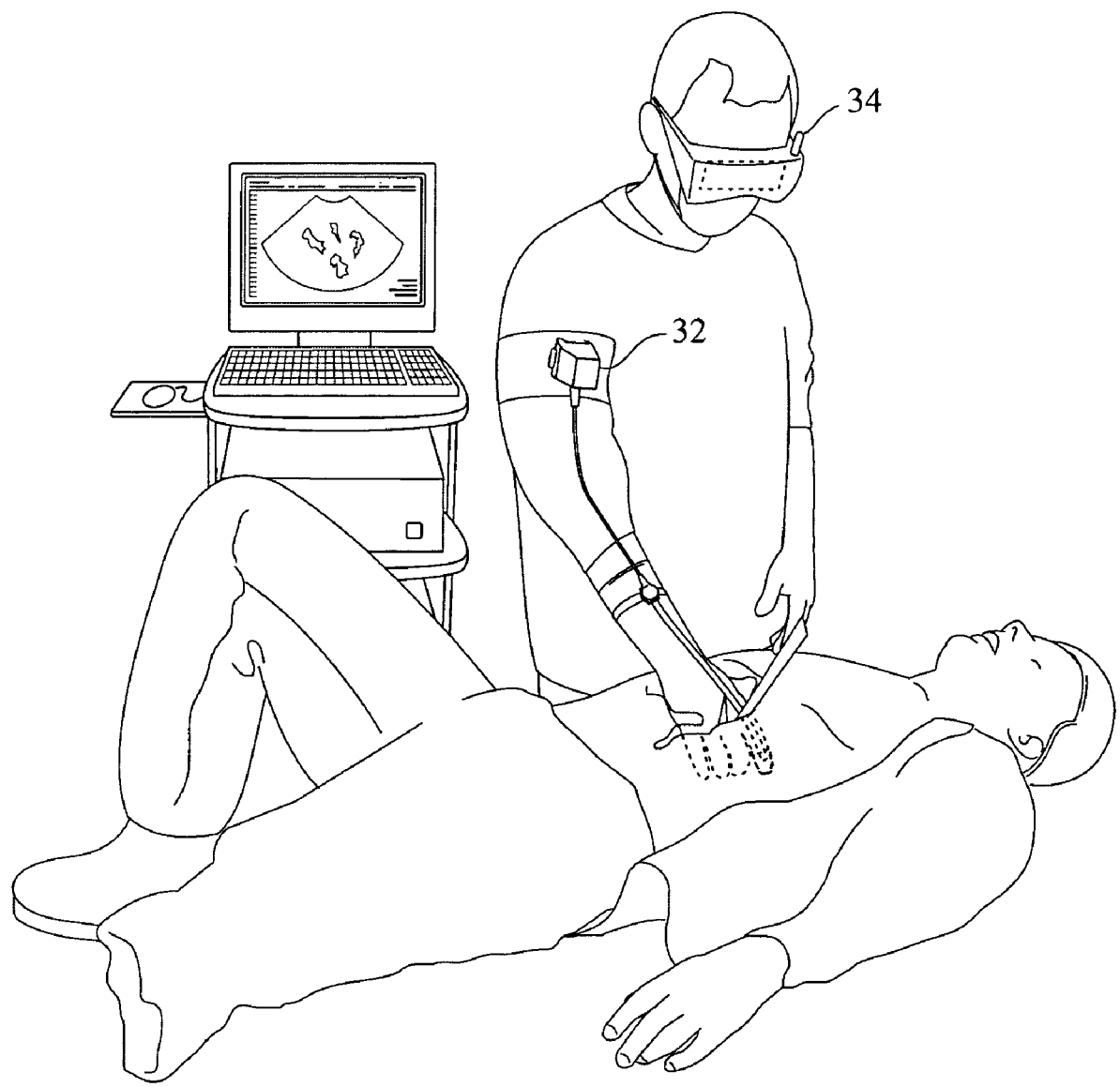
FIG. 3 is a perspective view of an alternative embodiment of the assembly of FIG. 1, having a wireless link to an imaging station, in use on a patient.
Figure 4:
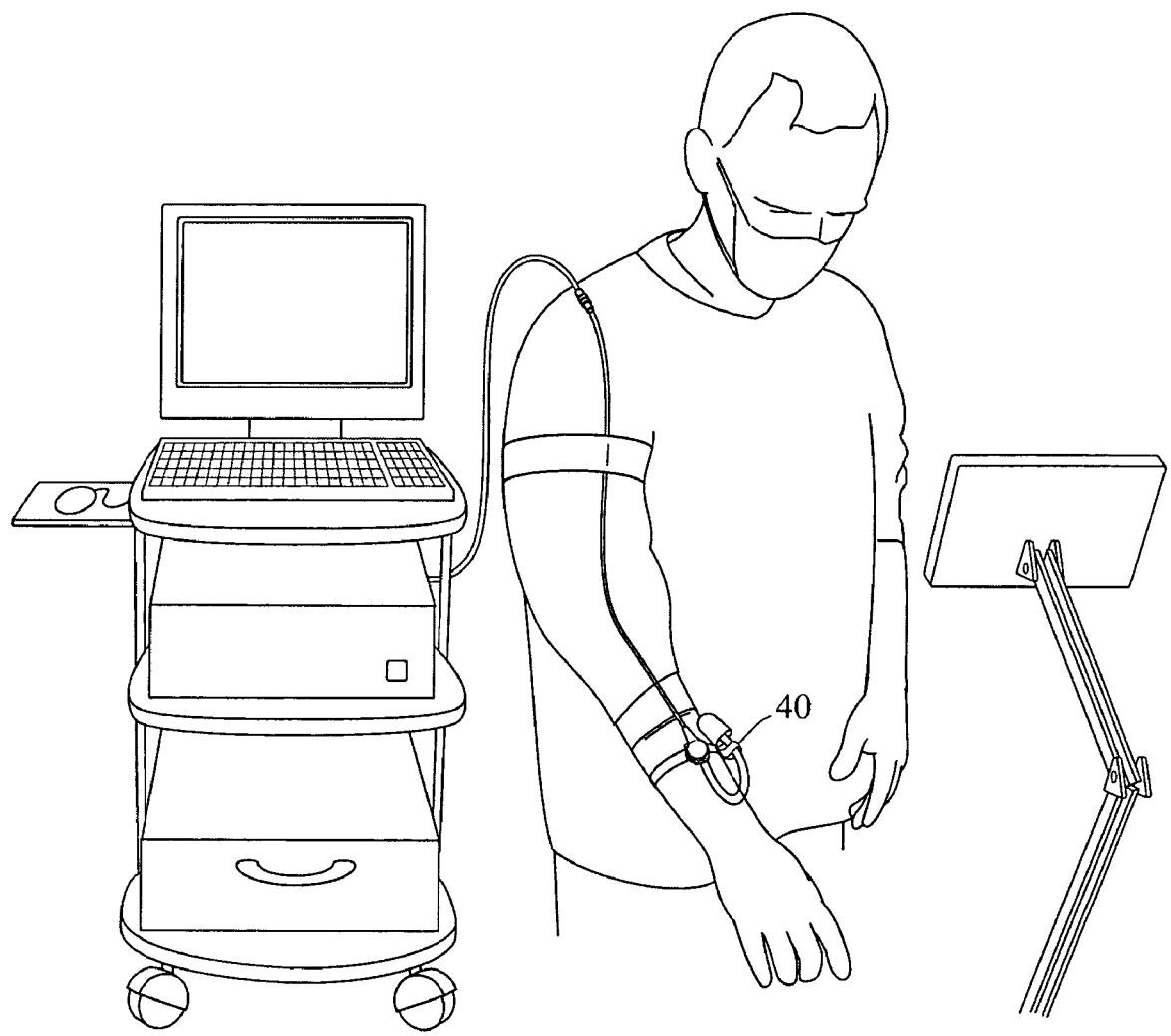
FIG. 4 is a perspective view of the assembly of FIG. 1, showing a probe retaining clasp, on the forearm unit, in use.

Referring to FIG. 3, in an alternative preferred embodiment a wireless link is established between sub-assembly 26 and imaging station 12. A data processing and transmission unit 32 receives the signals from probe 30 and extracts the imagery, thereby greatly reducing the volume of data to be transmitted. The imagery is transmitted, typically by RF, to imaging station 12 and/or to heads-up display goggles 34, which superimpose the imagery on the user's field-of-view. In an alternative preferred embodiment unit 32 is located directly on the wrist band 22. Referring to FIG. 4, in a preferred embodiment a catch 40 is provided on wrist band 22, for the purpose of retaining probe 30, so that it can be folded back, out of the way of the user's hand, when not in use. In an alternative preferred embodiment, catch 40 is implemented by a system of magnets, with mutually attractive magnets on wrist band 22 and probe 30. Probe sub-assembly 26 is made of light weight materials and has a mass of less than 70 grams. The distal 3 cm of probe 30, which includes the ultrasound transceiver, has a mass of about 11 grams. This low mass is very important in enabling a user to easily maneuver the probe 30.

Applicant notes, in connection with the immediately following discussion, that flex-circuit is a term of art in the electric device industry, referencing a connective element made of a sheet of polymeric dielectric material having conductive traces formed on it by photolithographic techniques. It may be sealed with an additional sheet of polymeric material, so that the conductive traces are interposed and sealed between the two sheets. Referring to FIGS. 5A-5C, in one preferred embodiment construction of sub-assembly 26 begins with the creation of a T-shaped piece of flex circuit 40. In an alternative preferred embodiment, two L-shaped pieces are placed side-to-side to form a T-shape. The length 46 between a proximal end 42 and a distal end 43, of flex circuit 40 is 25 cm. The length 48 of the T-shape top bar at distal end 43 is 2.5 cm. The distal end T-shape top bar is made of a first branch 44 and a second branch 45. Conductive traces 50, each turn at the T-junction and extend almost the entire extent from proximal end 42 to the end of either branch 44 or 45.

A set of bare trace ends 53 are formed at the free ends of branches 44 and 45 by removing the end of the plastic of flex circuit 40 from about traces 50, typically by laser ablation. An ultrasound transceiver is formed by connecting the trace ends 53, to a piece of piezoelectric material 56. After attachment, a high performance acoustically absorptive backing material 54 is affixed behind piezoelectric material 56, so that trace ends 53 are encapsulated between backing material 54 and piezoelectric material 56. Backing material 54 may be as disclosed in U.S. Pat. No. 4,779,244, issued Oct. 18, 1988, which is incorporated by reference as if fully set forth herein. In this patent a backing material having an acoustic absorbance equal to or greater than 60 db/cm/MHz is disclosed. Using such a material and given the need to attenuate a typical 5 MHz ultrasound signal emitted from the back of the array by approximately 150 dB through a two-way trip through the material (so as not to interfere with the image), the array backing would be approximately Xcm=150/(60 db/cm/Mhz*2*5 MHz)=2.5 mm, which provides a very low profile for a transducer to fit on the finger.

In instances where a high absorptive backing material is not available, such as for a pre-existing probe retrofit, such a probe could be modified by creating a toothed pattern, such as that found on the sides of an anechoic chamber, in the surface of the backing material that faces away from the ultrasound array. This causes the sound waves reflecting off the rear of the ultrasound array stack to scatter.

The piezoelectric material 56 is then patterned as shown, with each resultant element created by this patterning being connected to a unique trace 53. In a preferred embodiment, even ultrasound elements are connected to branch 44, while the interposed odd elements are connected to branch 45, or vice versa. Skilled persons will appreciate that the alternative method of construction noted above, in which two L-shaped pieces of flex circuit are used, rather than a single T-shaped piece, permits the step of connecting bare traces 53 to materials 54 and 56 to be performed with the two L-shaped pieces of flex circuit laying flat, thereby greatly easing this connective task. The two L-shaped pieces may then be curled up and joined at the top, thereby forming an annulus that fits about the finger.

Figure 11:
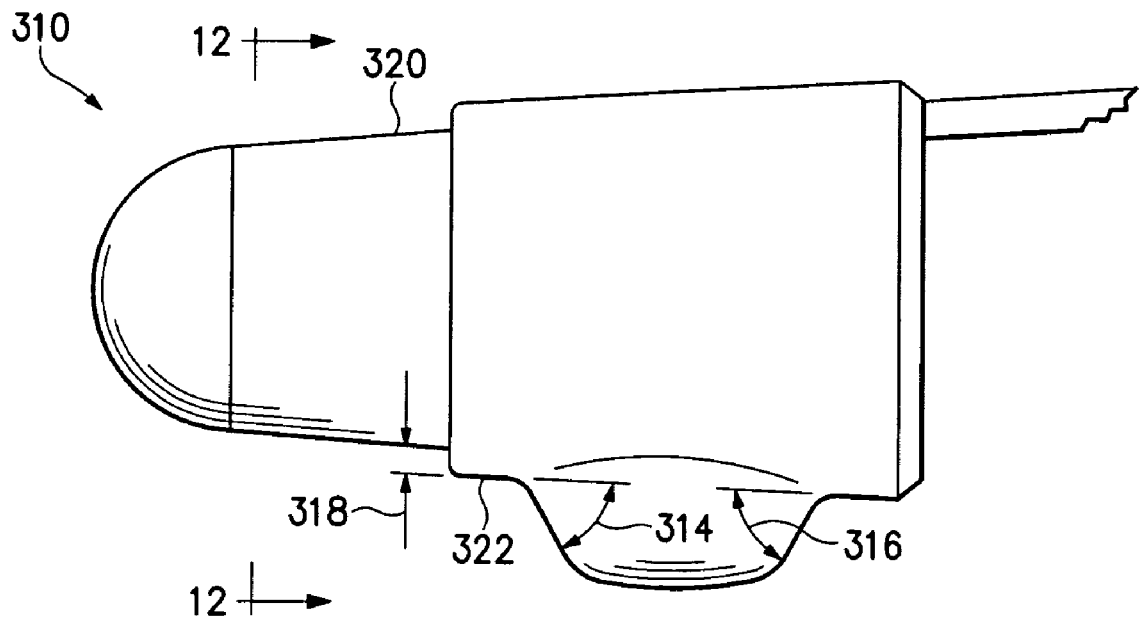
FIG. 11 is a side view of a finger mounted probe, defining an angle of interest.
Figure 12:
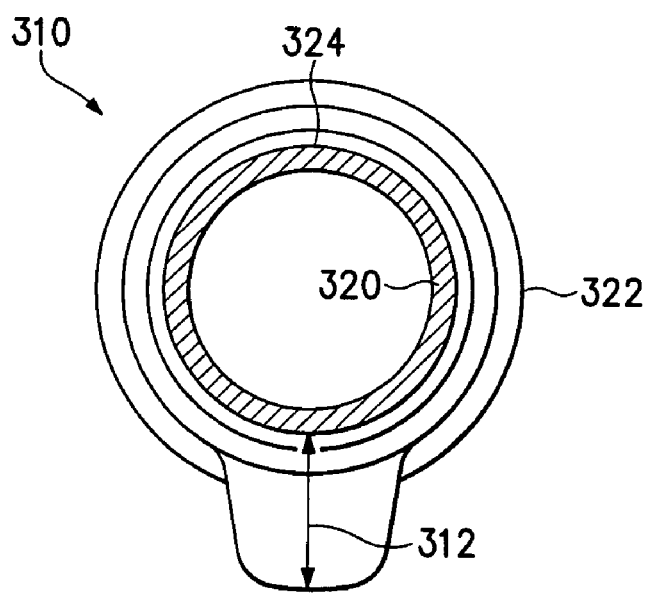
FIG. 12 is a front view of the probe of FIG. 11, showing a distance of interest.

Referring to FIG. 5C, the branches 44 and 45 are curved downwardly to fit about a finger, so that ultrasound array 56 now faces downwardly and is oriented to sweep from forward and backward relative to the finger. A housing is added about the ring that is formed by branches 44 and 45 and materials 54 and 56, to arrive at a final probe 30, such as is shown in FIGS. 7-10. A protective coating may be added to the medial portion of flex circuit 40. Referring to FIGS. 11 and 12, a probe 30 constructed according to the preferred methods described herein may have a distance 312 from the interior surface 324 of the finger mount to the furthest protrusion of the probe of about 1.2 cm, greatly facilitating a user in passing the probe 310 through tight passages in the body. In another embodiment distance 312 equals about 1.5 cm.

Moreover probe 30 is made in a preferred embodiment so that the ultrasound transceiver protrudes gradually outwardly (downwardly) from front to middle. Defining an angle 314, as the angle between a probe surface that extends parallel to the user's finger and the surface of the probe as it begins to protrude outwardly, angle 314 is about 70° at its maximum. In an alternative preferred embodiment, angle 314 is about 60° at its maximum and in yet another preferred embodiment, this angle is about 50° at its maximum. In yet another preferred embodiment, angle 314 is about 40°. An additional angle 316 may be defined as the angle between a probe surface that extends parallel to the user's finger and the surface of the probe as it begins to extend outwardly, going from rear to front. It is also desirable to minimize angle 316, so that as the probe is being removed back though tissue, it disturbs the tissue as little as possible. In a preferred embodiment this angle is about 40°. In other preferred embodiments this angle ranges from 40° to 70°.

A finger cot 320 is used to both isolate the front of the finger from tissue, provide a rounded surface at the front of the finger, which can be pushed through tissue with less chance of causing damage, and making it possible for a probe unit 310 having a fixed inner diameter 324 to accommodate a range of finger thicknesses, by providing a range of cots having different thicknesses. It is desirable to minimize the distance 318 between finger cot 320 and probe surface 322. Although this distance is shown as being on the order of 2 mm, in another preferred embodiment distance 318 is zero, with the finger cot 320 being flush with the probe surface.

This low profile and gradual protrusion greatly facilitates a probe user in inserting the probe into small body cavities and avoiding damage to delicate tissues. Along these lines it is beneficial to have a "bullet shaped" probe that comes to a point forward of the finger and smoothly expands to the area where the transponder is located. This can be accomplished by equipping the probe with a forward section that terminates distal to the finger tip in a single point and expands transversely outwardly approximately equally in each direction, to yield the bullet shape. The transceiver fits in the smooth housing.

In one preferred embodiment a 128 element probe is constructed and in an alternative preferred embodiment a 256 element probe is constructed. The probe head is completed by adding a lens and housing. Skilled persons will recognize that although a linear array is shown, a curved linear array could be constructed just as easily, using the techniques shown, simply by curving the piezoelectric material after it is diced. In an alternative preferred method of construction, a separately formed ultrasound transceiver is connected to flex circuit 40 by way of a flex circuit connective tab.

The use of a high absorptive backing material 54, incorporated into the array, as well as a method of construction that obviates the need for connecting the flex circuit to a cable in the probe head permits the formation of a lower profile probe head. As noted elsewhere in this document, this low profile is critical in permitting a user to locate the probe in tight spaces internal to the human body without damaging body tissue. The benefit of this innovation may be utilized in probes that do not otherwise fit the disclosure of this application. For example, flex circuit 40, rather than terminating in connector-half 24, can be terminated at a multi-conductor coaxial cable, of the type that is currently standard in the ultrasound imaging industry, 5 cm or more away from the probe with or without a connector. In the typical current probe design, the multi-conductor coaxial cable terminates quite close to the probe head or in the probe head, causing the finger-mounted portion to be bulky and heavy. By extending the flex circuit portion more than 5 cm from the probe itself, and preferably more than 10 cm or even 20 cm, the finger-mounted portion is kept light and given a low profile. Accordingly, the present invention is not limited to the system connectors that although advantageous do not by themselves yield the low profile of the probe.

In an alternative preferred embodiment a capacitive micromachined ultrasound transceiver (CMUT) is connected to traces 50, using the same techniques as used for connecting piezoelectric material 56. A CMUT transceiver tends to be thermally robust, thereby lending itself to use in a probe that may be exposed to the heat and pressure of an autoclave sterilization cycle, without being damaged.

Referring to FIGS. 5A-5C, at the proximal end 42 of work piece 40, a set of electrical contact points 52 are formed by removing the flex circuit plastic down to each trace 50, in a particular spot. Conductive material is deposited onto contacts 52, so that they are not recessed. Alternatively, a surface coating material covers flex traces so that only connector contacts 52 are left exposed on the surface of flex forming contacts 52. Rigid backing material 58 is adhered underneath the flex circuit and a metal housing (not shown) is provided to finished connector-half 22. Alternatively, the proximal end of the flex circuit can be selectively rigidized by laminating a rigid, circuit board material layer onto the flexible portion, and forming connections to the flex traces by laser or mechanical drilling and subsequent plating, to form a monolithic integrated connector assembly.

Figure 6:
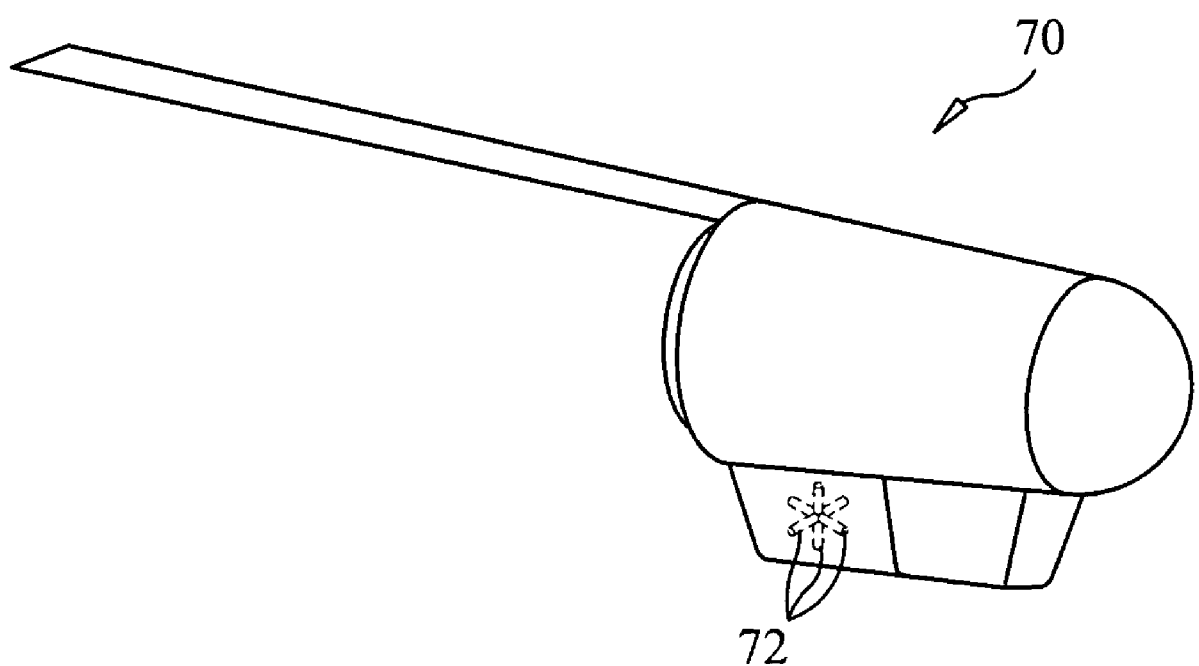
FIG. 6 is a side view of the finger probe of FIG. 1, showing navigational elements.

Referring to FIG. 6, in a preferred embodiment a finger probe 70 includes a set of accelerometers (not shown) and/or inductors 72 that are mounted in a mutually orthogonal pattern are provided as part of finger probe 30 to permit location determination while finger probe 30 is within the body and not directly observable.

Figure 7:
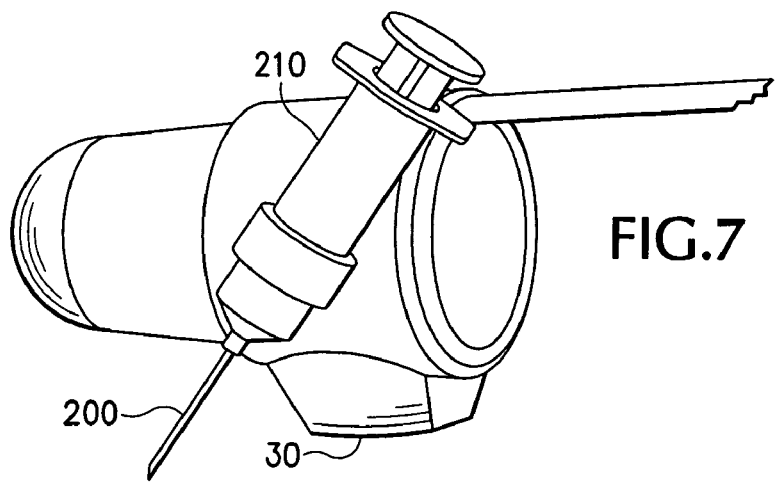
FIG. 7 is a perspective view of an alternative embodiment of the probe of FIG. 1, having a hypodermic needle attached.
Figure 8:
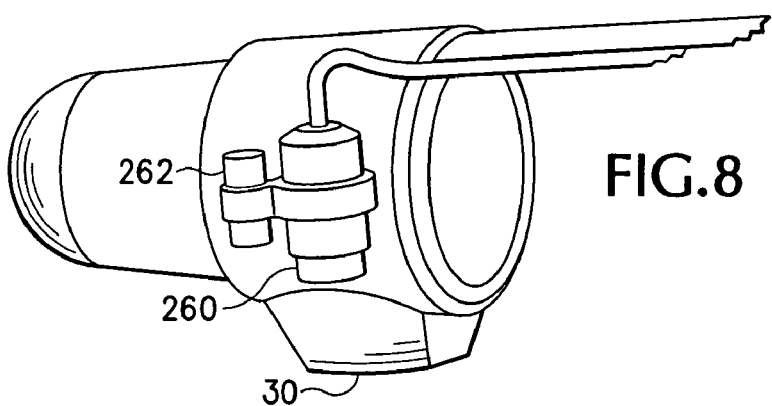
FIG. 8 is a perspective view of an alternative embodiment of the probe of FIG. 1, having an electric camera attached.

Referring to FIG. 7 in an additional preferred embodiment, a hypodermic needle 200 and an attached syringe 210 are releasably mounted adjacent finger probe 30. This permits imagery gathered by finger probe 30 to assist a health care professional in finding a blood vessel of interest. Health care professionals sometimes need to find a particular blood vessel, such as the jugular vein, in order to inject fluid or drugs as soon as possible so that the substance being injected will reach a target organ as quickly as possible. In such application, known as central-line-placement, color flow ultrasound imagery, in which Doppler flow information drives the display of the blood vessels and non-Doppler information drives the display for the surrounding tissue, is particularly useful in this endeavor. In an alternative preferred embodiment, another sort of skin broaching device, such as a canula (not shown) or a hypodermic needle connected, to an intravenous drip bag is associated to the ultrasound probe. Guidance of the hypodermic needle associated with the finger probe may also be assisted by use of commercially available guidance devices, such as a pressure sensor associated with the needle, including that available from Vascular Technologies, Ness-Ziona, Israel, which provide an additional positive indication when the needle enters a vein, through sensing a pressure change.

An additional preferred embodiment is the same as described above except for that an optical link 260 and light source 262 is provided to permit optical viewing of body tissue. In one preferred embodiment the optical link 60 is in the form of a lens coupled to a fiber optic link on probe 30 that may terminate in a video camera. Alternatively optic link 260 is in the form of a video camera (as shown) attached to the finger probe 30 and adapted to communicate electrically with the imaging station 12, or heads up display 34. In either situation it is necessary to provide light for the optical link 260. This is accomplished either by an electrically powered light source, such as a light emitting diode 262, or a chemically powered light source (not shown), such as those available under the trade name "pin lights," from Embo-Optics of Beverly, Mass.

Figure 9:
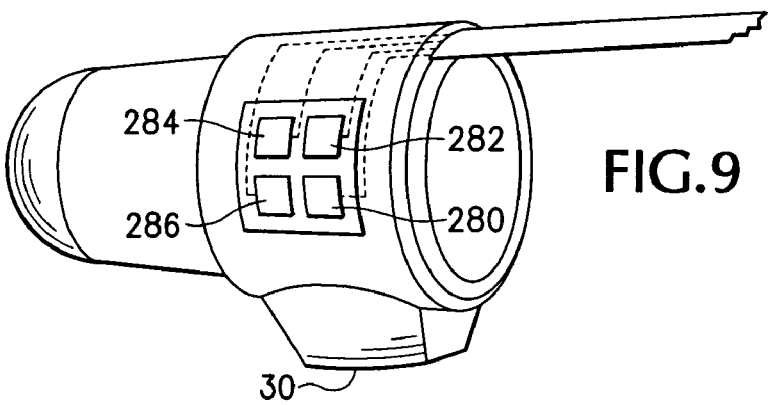
FIG. 9 is a perspective view of an alternative embodiment of the probe of FIG. 1, having a set of sensors attached.
Figure 10:
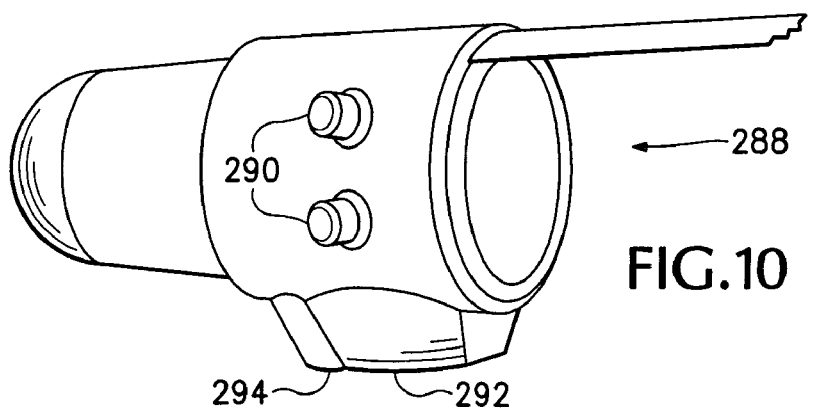
FIG. 10 is a perspective view of an alternative embodiment of the probe of FIG. 1, having a set of controls attached.

Referring to FIG. 9, in another preferred embodiment a finger probe, such as 30, is equipped with a sensor suite that includes a thermometer 280, an oximeter 282, a pressure sensor 284 and a glucometer 286. In an alternative embodiment element 286 is an agent administration patch 286 that is electrically activated by a trace 50 to express the agent, thereby administering the agent to a precise location. In an alternative preferred embodiment, a smaller set of sensors is provided, or even a single sensor only.

In another preferred embodiment, a finger assembly 130 is provided that can both image tissue, using ultrasound, and that can also provide therapy, typically by cauterizing tissue, also using ultrasound. First there is an assembly 288 that includes both an imaging array 292 and a treatment array 294. The treatment array uses up to 100 watts of power and is powered by traces that are larger in cross-sectional dimension and are therefore capable of conducting more current if order to meet the greater power demands of treatment array 294. In an alternative embodiment a smaller number of sensors, or just one sensor, are available.

In another preferred embodiment of an ultrasound assembly (not shown), a single array is used for both imaging and treatment. In one variant of this embodiment, some piezoelectric elements are used for both imaging and treatment and others are used solely for imaging. Again, the array must be powered by a larger input of current and to accommodate this need, larger traces 40 (FIG. 5A) are provided for the treatment ultrasound elements.

A set of thumb controls 290 are provided for probe 288, so that the user may switch between imaging and treatment. These controls are typically in the form of a small push button that must be pressed in a specific pattern, for example two rapid presses followed by continuous pressure during the period of time treatment is desired, in order to activate treatment mode, as any inadvertent activation could greatly harm a patient. In one preferred embodiment a warning signal is given when two rapid presses have placed the treatment probe in a "ready" state, in case some passage through tissue ever causes two rapid presses to occur. In an alternative preferred embodiment controls are placed on the wrist or forearm band 22, thereby providing easy access for a probe user.

In another preferred embodiment, buttons 290 are provided for a probe, such as probe 30, in which therapeutic ultrasound is not available. The buttons are instrumented to change the scan width and orientation; the transmit power and frequency; and imaging mode among other quantities. The buttons 290 communicate with imaging station 12 by way of traces 50 and cables 18 and 14 or by RF transmission in the embodiment of FIG. 3. The buttons 290 may also communicate or be mechanically associated with the array within the finger probe to allow a change in orientation of the array elements to effect the orientation of the scan plane.

One use of probe 30 is for the intra-operative evaluation of plaque deposits in the aortic arch and ascending aorta, prior to accessing the aorta. To perform this function a Doppler probe may be used and a measurement of the speed of the blood in the aorta formed. In the case where the aorta has been narrowed due to plaque deposits, the blood flows more rapidly. The accessing of the tissue of the aorta is greatly eased by use of a finger mounted probe, as opposed to the long, stiff intra-operative probes currently available.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A finger mountable sensor assembly comprising:
   (a) a finger mountable housing having a palmar aspect and including a finger receptacle, the finger receptacle having a dorsal aspect;
   (b) an ultrasound transceiver located on said finger receptacle on said palmar aspect of said housing;
   (c) a T shaped assembly comprising three branches of electrically conductive material, wherein said first branch and said second branch extend around said finger receptacle from said ultrasound transceiver to said dorsal aspect of said finger receptacle; and
   (d) said third branch of electrically conductive material extends away from said dorsal aspect of said finger receptacle; and
   (e) wherein said third branch of electrically conductive material is interconnected electrically with said sensor assembly transceiver by being interconnected electrically with said first and second branches in a location which is proximal to said dorsal aspect of said finger receptacle.

2. The sensor assembly of claim 1 wherein said branches comprises flex circuit.

3. The sensor assembly of claim 1 wherein said branches comprises ribbon cable.

4. The sensor assembly of claim 1 wherein said branches resides inside said housing.

5. The sensor assembly of claim 1 including a connector half, and wherein said electrically conductive material terminates in and extends to said connector half from said arc.

6. The sensor assembly of claim 1, wherein said electrically conductive material terminates in a sterilizable connector assembly.

7. The sensor assembly of claim 1 wherein said electrically conductive material is a ribbon cable.

8. The sensor assembly of claim 1 wherein said finger receptacle has an interior surface adapted to contact a human finger, and wherein said ultrasound transceiver protrudes outwardly, relative to said interior surface, by less than 1.5 cm.

9. The finger mountable sensor assembly of claim 1 wherein said finger receptacle has a pair of opposite lateral sides and each said branch of conductive material includes on each said lateral side of said finger receptacle at least one respective electrical conductor extending from said ultrasound transceiver to said dorsal aspect of said finger receptacle.

10. A finger mountable sensor assembly comprising:
    (a) a finger mountable housing having a palmar aspect and a dorsal aspect and including a finger receptacle;
    (b) an ultrasound transceiver located on said palmar aspect of said housing comprising a piezoelectric material and an acoustically absorptive backing material;
    (c) two branches of electrically conductive material connected to said ultrasound transceiver, said branches extending around said finger receptacle within said housing to the dorsal aspect of said housing, thereby adapted to encircle a user's finger located within said finger receptacle, wherein said two branches connected to said transceiver form a ring;
    (d) a third branch of electrically conductive material extending away from the dorsal aspect of said housing; and
    (e) wherein said third branch of electrically conductive material is interconnected electrically with said transceiver by being interconnected electrically with said two branches.

11. The finger mountable sensor assembly of claim 10 wherein said branches of electrically conductive material form a T shape.

12. The finger mountable sensor assembly of claim 10 wherein said branches of electrically conductive material form two L shapes.

13. The finger mountable sensor assembly of claim 10 wherein said branches of electrically conductive material comprise flex circuit.

14. The finger mountable sensor assembly of claim 10 wherein said branches of electrically conductive material comprise cable.

15. The finger mountable sensor assembly of claim 10 wherein said third branch of electrically conductive material comprises cable.

16. A finger mountable sensor assembly comprising:
    (a) a finger mountable housing having a palmar aspect and a dorsal aspect and including a finger receptacle;
    (b) an ultrasound transceiver located on said palmar aspect of said housing; and
    (c) an assembly of electrically conductive material having three branches, wherein two said branches connect to said transceiver and extend around said housing, and are thereby adapted to encircle a finger located within said receptacle, and one said branch emerges from and extends away from said dorsal aspect of said housing.

* * * * *